United States Patent [19]

Galel

[11] Patent Number: 5,492,131
[45] Date of Patent: Feb. 20, 1996

[54] SERVO-CATHETER

[75] Inventor: Zev Galel, Palo Alto, Calif.

[73] Assignee: Guided Medical Systems, Inc., Mountain View, Calif.

[21] Appl. No.: 301,319

[22] Filed: Sep. 6, 1994

[51] Int. Cl.⁶ .................................................. A61B 5/10
[52] U.S. Cl. ...................... 128/772; 600/114; 600/145; 600/146
[58] Field of Search ................................. 128/6, 657, 658, 128/772; 604/95, 280–283; 33/511, 512

[56] References Cited

U.S. PATENT DOCUMENTS

| | | | |
|---|---|---|---|
| 4,292,961 | 10/1981 | Kawashima | 33/512 |
| 4,758,222 | 7/1988 | McCoy | 128/657 |
| 5,064,415 | 11/1991 | Walder et al. | 604/164 |
| 5,188,111 | 2/1993 | Yates et al. | 128/657 |
| 5,238,005 | 8/1993 | Imran | 128/772 |
| 5,274,551 | 12/1993 | Corby, Jr. | 128/654 |
| 5,346,498 | 9/1994 | Greelis et al. | 606/108 |
| 5,389,073 | 2/1995 | Imran | 128/772 |

*Primary Examiner*—Max Hindenburg
*Attorney, Agent, or Firm*—Townsend and Townsend and Crew

[57] ABSTRACT

A catheter is guided by directional control inside a bodily passage by a servo-type system which includes a sensor to transmit position, orientation or velocity information to a microprocessor which is typically programmed with an error detection algorithm, and a motion control system. The motion control system generates a signal representative of the change in position, orientation or velocity needed to guide the catheter along a prescribed course of travel or in general to continuously adjust its position relative to a target, and this signal is transmitted to a directional steering system, a forward drive system or both, to effect the change. The result is a closed-loop servo system capable of automated, preprogrammed advancement and/or positioning of the distal catheter tip through branched and convoluted passages to a site where therapeutic action is needed or from which diagnostic information is sought.

6 Claims, 1 Drawing Sheet

SERVO-CATHETER

This invention resides in the field of medical catheters, and relates in particular to means for automatic and semi-automatic steering of catheters inside bodily passages.

BACKGROUND OF THE INVENTION

Catheters are used in various different medical procedures and are a common tool in the health care industry. Even though catheters are generally disposable, many catheters contain sophisticated functional devices for use inside the body. These devices include a wide range of sensors, cutting or ablating devices, and the like, and are used for performing various types of diagnostic and therapeutic functions. Catheters are also used to convey fluids into and out of the body.

Since the function performed by a catheter is generally performed at its distal tip, i.e., the tip furthest inside the patient's body and furthest away from the catheter operator, the position of the distal tip, its orientation, or both are often critical to the success of the procedure. Examples of catheter procedures in which improper positioning of the tip can impair the effectiveness of the procedure are as follows:

Cardiovascular procedures, used as an alternative to bypass surgery for the removal of plaque from arteries: the incomplete removal of plaque is partially responsible for restenosis (recurrence of blockages previously treated), which occurs in approximately 25% of cases;

Vascular procedures, used for the removal of plaque or thrombi from peripheral arteries such as the carotid arteries and the arteries in the legs;

Obstetrics/gynecological procedures, where catheters are used for the selective removal of excessive tissue and cyst growth, and for the delivery of site-specific treatments for ovarian cancer;

Urological procedures, where catheters are used for the selective removal of prostate cancer, and for the treatment of urinary tract blockages;

Oncological procedures, where catheters are used for the selective removal of malignant tissue, without harming adjacent healthy tissue, and for performing biopsies in a manner which entails a minimum of trauma in the surrounding tissue;

Neurosurgery, where catheters are used for the precise removal of intracranial hematoma;

Radiology, where guided catheters are used to achieve active stabilization within the cardiac chamber for imaging and mapping; and Internal procedures in general, such as those where guided catheters are used for fluid aspiration to relieve abscesses, or for localized drug delivery.

In procedures involving sensing and diagnosis, an error in the orientation of the catheter may cause a false reading. In procedures involving the delivery of high concentrations of medication to narrowly delineated sites, the effectiveness of the medication and the minimization of side effects can depend on how precisely the delivery site can be targeted. In procedures involving the removal of diseased tissue by cutting or ablation, proper positioning and orientation of the tip are critical in achieving complete removal of the diseased tissue without harm to healthy neighboring tissue.

Since the point of insertion of the catheter into the body is usually a considerable distance from the target site, it is difficult to attain proper positioning of the catheter tip. To address this problem, various remote control mechanisms have been incorporated into catheter designs, but there is much room for improvement, particularly for catheters which contain highly sophisticated and powerful therapeutic devices and whose functions are needed at sites which are particularly difficult to reach. As catheters become more complex, the need for precise directional control increases.

These and other problems are addressed by the present invention.

SUMMARY OF THE INVENTION

This invention resides in a closed-loop servo-type system for guiding a catheter into or through a bodily passage or positioning a catheter within a bodily passage. The invention is an integration of several components:

a sensor which provides data representing one or more motion parameters of the distal tip of the catheter, such as the position, orientation, or velocity of the tip, including related parameters such as distance from the wall of the bodily vessel or acceleration of the tip;

a control system preferably including a microprocessor and a motion control system, the microprocessor receiving the data from the sensor and comparing the data to a target value, such as to determine position error as the difference between the desired (target) and the actual (sensor-detected) position, and the motion control system being a system which keeps the position error to a minimum at all times by providing motion commands for transmission to the distal end of the catheter; and a drive or directional control system which receives the motion commands from the motion control system and causes the distal tip of the catheter to move in accordance with the commands.

The sensor may be internal or external to the patient's body. The data provided by the sensor may be data such as position, displacement, velocity, acceleration, a two-dimensional image, a three-dimensional image, or any other such parameter or set of parameters. The data can range from a numerical value for a single parameter such as velocity, distance, or displacement from the vessel wall, to a complex set of data for a three-dimensional image of the interior of the bodily vessel in the region of the catheter tip. An example of an internal sensor is one which generates a signal at the catheter tip, or a series of signals from which an image can be generated, and conveys the signals along the catheter itself to the motion control system for processing. An example of an external sensor is one in which energy is emitted from the catheter tip at a continuous level, such as by a radiopaque or fluoroscopic marker embedded in the tip. The location of the emission source, and hence the catheter tip, may for example be visualized by a receptor screen outside the body. The image is then processed and transmitted to the motion control system.

The microprocessor may be part of a personal computer or a central processing unit, or analogous systems. The target value with which the microprocessor will compare the sensor data may for example be a value representing a prescribed course or path of travel through the bodily vessel or a prescribed distance between the catheter tip and the vessel wall.

The motion control system may be a system which simply compares a sensed value to a single target counterpart, determines the error and emits a proportional corrective signal whose magnitude corresponds to the degree of correction indicated. In more advanced embodiments, the motion control system may receive two- or three-dimensional imaging information from the sensor, and convey signals for directional movement of the catheter tip in two or three dimensions, including forward thrusts and lateral thrusts for steering purposes.

The drive or directional control system may produce directional changes in the catheter tip to conform to the curvature of the bodily vessel, urge the catheter tip forward for advancement into the vessel, or both. The forces are preferably those which are generated at the catheter tip itself upon appropriate signals from the motion control system.

Additional features and advantages of the invention will become apparent from the description which follows.

BRIEF DESCRIPTION OF THE DRAWING

The drawing attached hereto is a block diagram of an illustrative servo-type catheter system in accordance with the present invention.

DETAILED DESCRIPTION OF THE INVENTION AND PREFERRED EMBODIMENTS

Figure 1:
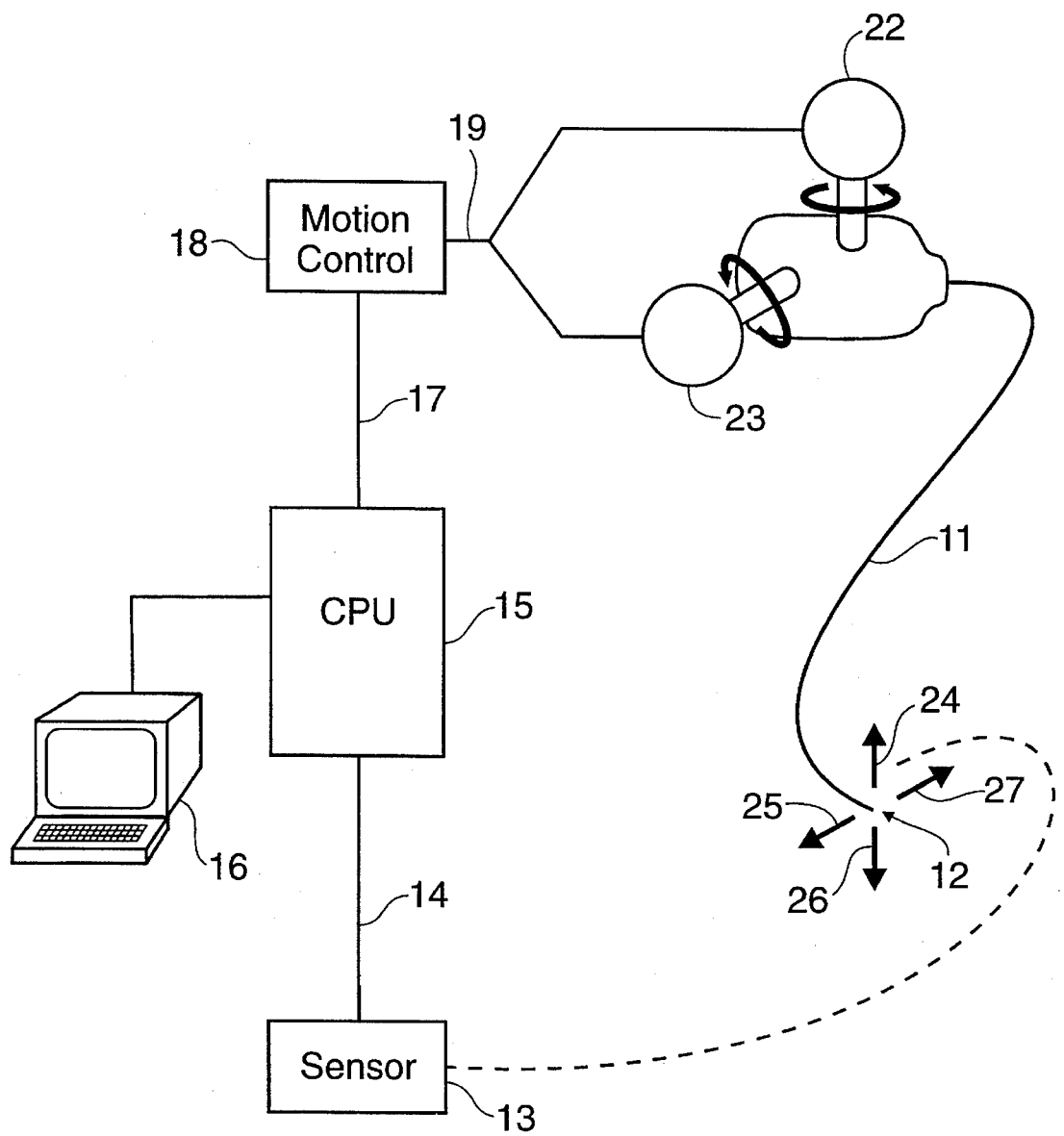

Sensing elements for incorporation into the catheter tip in accordance with this invention may be any of the various types used in the medical catheter industry or described in the literature. Radiopaque markers are a common example of a sensing element. Examples of radiopaque markers are rings or coils of gold or platinum. Ultrasonic imaging is another example, achieved by the placement of an ultrasonic transducer at the catheter tip or external to the body. Examples of ultrasonic transducers are piezoelectric crystal oscillators and organic electrets such as polyvinylidene difluoride. One example of an ultrasound system is INSIGHT®, a product of Cardiovascular Imaging Systems, Inc., Sunnyvale, Calif., U.S.A. A further example is fluoroscopic imaging, achieved by the placement of a contrast medium at the catheter tip, or by perfusing a contrast medium through the catheter tip into the surrounding region. Imaging can also be achieved by the use of fiber optic bundles, real-time x-ray, CT-scanning or magnetic resonance imaging.

Motion control systems suitable for use in this invention vary widely. Examples of systems and key components of the systems are stand-alone motion controllers, both single-axis and multi-axis, piezoelectric micropositioners, piezo-driven stages, X-Y positioning stages, controllers with input formats which are either of the CNC, DX or raster types, PC-based controllers, bus-compatible controllers, and MOS-FET PWM servo amplifiers and motor drives. Suppliers of these and similar components include Motion Science Inc., San Jose, Calif.; Polytec Optronics, Inc., Costa Mesa, Calif.; Motion Engineering, Inc., Santa Barbara, Calif.; Adept Technology, Inc., San Jose, Calif.; Emerson Electronic Motion Controls, Chanhassen, Minn.; and Allen-Bradley Company, Lebanon, NH.

For directional control, a wide variety of steering systems to orient the distal tip of the catheter from the proximal end may be used. One example of such a system is the use of tensioning members or deflection wires which extend along the length of the catheter and are selectively tensioned at the proximal end to bend the distal tip in a selected direction. Another example is one which uses a temperature-activated memory element which is embedded in the distal end and assumes a curvature upon reaching a threshold temperature, the temperature control being achieved by electrical heating. A third example is the use of fluid pressure in enclosed passages within the catheter in the vicinity of the distal end, the pressure causing a curvature of the catheter. A fourth example is the use of directional jets emitted by nozzles at the distal end to produce lateral thrust from the reaction force of a selected jet. Among the suppliers of directional control systems of these and other types are EP Technologies, Inc., Mountain View, Calif.; Medtronic Cardiorhythm, San Jose, Calif.; and Versaflex Delivery Systems, Inc., San Diego, Calif. Steering systems which are mechanically driven can be driven by a variety of common units, such as servo motors. Depending on the type of control required, the system may contain a single servo motor, or two or more in orthogonal directions.

The integration of these components into the present invention results in a closed-loop system which can serve one or more of the following functions:

(1) The system can be used to provide a catheter which can navigate itself through the body, along a prescribed course of travel to a designated destination within the patient's body, in a fully automated manner.

(2) The system can be used to automatically maintain the distal end of the catheter at a fixed position relative to targetted tissue despite mechanical or fluidic disturbances in or surrounding the catheter system which would otherwise cause displacement of the distal end. This is important in a variety of therapeutic procedures. Examples are the firing of a laser into diseased tissue, the local delivery of drugs, and the use of a temporary pacemaker lead in a turbulent environment inside the heart.

(3) The system can be used to implement steering commands from the operator on a real-time basis, particularly commands which change frequently, and responding accurately to these commands even in the presence of external disturbances. This is particularly useful in cases where in situ process control is needed. For example, a ruptured artery will cause a catheter to retract automatically, and the system of this invention can compensate for the retraction.

(4) The system can be used to direct the catheter from a remote command station based on a transmitted visual image. A tele-operated catheter can enable the operator to guide the catheter from a control position which is remote from the patent. Further applications include the ability to follow the contour of a local lesion, where the exact shape of the lesion is not known in advance, and to perform selective cutting or selective drag delivery along or within the contour. In general, the invention will permit the replacement of manual steering mechanisms currently known with a high-precision electronic mechanism.

Turning now to the drawing, a catheter 11 is shown, which has a distal end 12 in which can be detected by a sensor 13 of any of the types described above. In this particular example, the sensor 13 is located outside the patient's body. The sensor 13 transmits data 14 representing the actual position of the catheter tip to a central processing unit 15. In this example, the CPU has a user interface 16 for operator-assisted control. Position error 17 is determined by the CPU by a conventional error program which determines the position error as the difference between the actual position and a pre-established target position based in part in this example on input from the user interface. The CPU 15 then transmits a representative signal to the motion control system 18 which generates and transmits a motion command 19 in accordance with the position error. The motion command 19 is received by a steering system which in this case consists of two servo motors 22, 23 which are located at the proximal end of the catheter but actuate a steering mechanism at the distal end. The servo motors cause the distal catheter tip 12 to bend in any of four orthogonal directions 24, 25, 26, 27 for steering purposes, as well as intermediate directions by combined vectors of adjacent orthogonal directions.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A closed-loop servomechanism for advancing a catheter through a bodily passage of a patient, said servomechanism comprising:

sensing means for generating a sensing signal indicative of a parameter selected from the group consisting of position, orientation and velocity of the distal tip of said catheter inside said bodily cavity in a substantially continuous manner;

control means for receiving said sensing signal, for comparing said sensing signal to a preselected program of target signals defining a target course of travel for said catheter to detect error relative to said target course, and for generating a corrective signal representative of a change calculated to reduce said error and thereby cause said catheter to travel in substantial conformance with said target course; and directional drive means for receiving said corrective signal and for imparting thrust at said distal tip of said catheter in a specified direction in accordance with said corrective signal.

2. A closed-loop servomechanism in accordance with claim 1 in which said sensing means includes a component remaining external to said patient when said catheter is inside said bodily passage.

3. A closed-loop servomechanism in accordance with claim 1 in which said sensing means comprises a member selected from the group consisting of radiopaque markers, ultrasonic transducers and optical fibers.

4. A closed-loop servomechanism in accordance with claim 1 in which said control means comprises at least one computer-driven servo motor governing movement of said distal tip in a selected direction.

5. A closed-loop servomechanism in accordance with claim 1 in which said control means comprises a pair of computer-driven servo motors, each said motor governing movement of said distal tip in a direction transverse to the longitudinal axis of said catheter and orthogonal to each other.

6. A closed-loop servomechanism in accordance with claim 1 in which said directional drive means is a member selected from the group consisting of tension wires, fluid jets, and temperature-actuated memory elements.

* * * * *